United States Patent
Yu et al.

(10) Patent No.: US 11,186,546 B2
(45) Date of Patent: Nov. 30, 2021

(54) METHOD FOR PREPARING 2,3-DICHLORO-5-TRIFLUOROMETHYLPYRIDINE WITH HIGH SELECTIVITY

(71) Applicants: Zhejiang Lantian Environmental Protection Hi-Tech Co., Ltd., Hangzhou (CN); Zhejiang Research Institute of Chemical Industry Co., Ltd., Hangzhou Zhejiang (CN); Sinochem Lantian Co., Ltd., Hangzhou (CN)

(72) Inventors: Wanjin Yu, Hangzhou (CN); Shengda Lin, Hangzhou (CN); Minyang Liu, Hangzhou (CN); Wucan Liu, Hangzhou (CN); Jianjun Zhang, Hangzhou (CN); Xianjin Chen, Hangzhou (CN)

(73) Assignees: Zhejiang Lantian Environmental Protection Hi-Tech Co., Ltd., Hangzhou (CN); Zhejiang Research Institute of Chemical Industry Co., Ltd., Hangzhou (CN); Sinochem Lantian Co., Ltd., Hangzhou (CN)

( * ) Notice: Subject to any disclaimer, the term of this patent is extended or adjusted under 35 U.S.C. 154(b) by 0 days.

(21) Appl. No.: 16/620,763

(22) PCT Filed: Dec. 5, 2018

(86) PCT No.: PCT/CN2018/119312
§ 371 (c)(1),
(2) Date: Dec. 9, 2019

(87) PCT Pub. No.: WO2019/109936
PCT Pub. Date: Jun. 13, 2019

(65) Prior Publication Data
US 2020/0102273 A1    Apr. 2, 2020

(30) Foreign Application Priority Data

Dec. 6, 2017 (CN) .......................... 201711275197.X
May 1, 2018 (CN) .......................... 201810009294.2
May 1, 2018 (CN) .......................... 201810009301.9
May 1, 2018 (CN) .......................... 201810020465.1

(51) Int. Cl.
*C07D 213/61*    (2006.01)

(52) U.S. Cl.
CPC .................. *C07D 213/61* (2013.01)

(58) Field of Classification Search
CPC .................................................. C07D 213/61
See application file for complete search history.

(56) References Cited

U.S. PATENT DOCUMENTS 4,288,599 A    9/1981    Nishiyama et al.
4,420,618 A    12/1983   Yokomichi et al.

FOREIGN PATENT DOCUMENTS

CN    104610137 A    5/2015
EP       007841 A2    5/1983

*Primary Examiner* — Noble E Jarrell
(74) *Attorney, Agent, or Firm* — Muncy, Geissler, Olds & Lowe, P.C.

(57) ABSTRACT

The present invention discloses a method for preparing 2,3-dichloro-5-trifluoromethylpyridine, comprising at a temperature of 100~150° C. and a pressure of 0.5~5.0 MP, in presence of at least one catalyst selected from supported metal chloride, supported zeolite molecular sieve and supported heteropolyacid, 2-chloro-5-trifluoromethylpyridine reacts with chlorine gas to obtain 2,3-dichloro-5-trifluoromethylpyridine. The preparing method provided by the present invention has advantages such as high selectivity of desired product, high utilization rate of chlorine gas, moderate process condition, simple operation and less three wastes. The present invention also discloses a preparing method for preparing 2-chloro-5-trifluoromethylpyridine, which is capable of reducing unit consumption, reducing separation cost, and improving safety compared to the prior art.

11 Claims, No Drawings

METHOD FOR PREPARING 2,3-DICHLORO-5-TRIFLUOROMETHYLPYRIDINE WITH HIGH SELECTIVITY

TECHNICAL FIELD

The present invention relates to a method for preparing chlorotrifluoromethylpyridine, specifically it relates to a method for preparing 2,3-dichloro-5-trifluoromethylpyridine.

BACKGROUND

Fluorine-containing, heterocycle, and chirality are three big features of the modern agricultural chemicals and new drugs in the medicine field. In recent years, new agrochemicals of fluorine-containing pyridines, such as chlorfluazuron, fluazuron, haloxyfop and fluazinam etc. have advantages such as broad-spectrum and systemic, high efficiency and low toxicity, and less pollution, thus they have become the major varieties of the highly efficient pesticide, herbicide and fungicide. 2,3-dichloro-5-trifluoromethylpyridine (2,3,5-DCTF) is a key intermediate for producing these new agrochemicals, it has become a hot point of the industry.

For the synthesis of 2,3-dichloro-5-trifluoromethylpyridine, there exists the following disclosures in the prior art:

(1) European Patent EP0078410 reports a method, wherein a fluidized bed is used as a reactor, in presence of $FeCl_3$/AC catalyst, a chlorination reaction takes place at 250° C. between 2-chloro-5-trifluoromethylpyridine and chlorine gas, to produce 2,3-dichloro-5-trifluoromethylpyridine. The yield of this method can reach 74%, but multiple isomers are produced in a gas phase chlorination reaction, as a result the products are difficult to separate;

(2) U.S. Pat. No. 4,420,618 reports a method for preparing 2,3-dichloro-5-trifluoromethylpyridine by an atmospheric liquid phase chlorination process, wherein in presence of a metal chloride catalyst, 2-chloro-5-trifluoromethylpyridine reacts with chlorine gas to produce 2,3-dichloro-5-trifluoromethylpyridine. The yield of this method is 16~75%, the catalyst amount is very large and needs to reach 40~200% of mass of the raw material, it is required to continuously introduce chlorine gas during the reaction process, the utilization efficiency of chlorine gas is low, resulting in a high production cost.

In the disclosed prior art, the gas phase chlorination method has disadvantages such as low selectivity of 2,3-dichloro-5-trifluoromethylpyridine, much of by-product isomers, difficulty to separate, and the liquid phase chlorination method has disadvantages of large catalyst amount, low chlorine gas utilization rate. Therefore, it is necessarily make further improvements to the preparing method of 2,3-dichloro-5-trifluoromethylpyridine.

SUMMARY

In view of the shortcomings of the prior art, the present invention provides a method for preparing 2,3-dichloro-5-trifluoromethylpyridine by a pressurized liquid phase chlorination, the method has characteristics such as high selectivity of desired product, high utilization rate of chlorine gas, moderate process condition, simple operation and less three wastes.

The names and abbreviations of the raw materials and products according to the present invention are as follows:
2,5-CTF: 2-chloro-5-trifluoromethylpyridine;
3,5-CTF: 3-chloro-5-trifluoromethylpyridine;
2,3,5-DCTF: 2,3-dichloro-5-trifluoromethylpyridine;
2,6,3-DCTF: 2,6-dichloro-3-trifluoromethylpyridine;
2,3,6,5-TCTF: 2,3,6-trichloro-5-trifluoromethylpyridine.
3-TF: 3-trifluoromethylpyridine;
3-MP: 3-methylpyridine;
2,3-CTF: 2-chloro-3-trifluoromethylpyridine;

For the preparing method provided by the present invention, its chemical reaction formula is as follow:

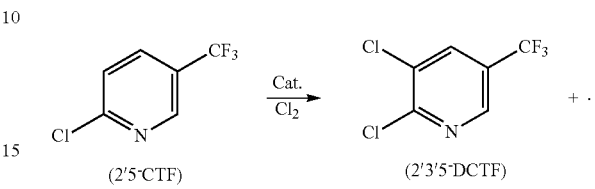

The present invention provides a technical solution as follow:

A method for preparing 2,3-dichloro-5-trifluoromethylpyridine, the method comprises:

At a temperature of 100~150° C. and a pressure of 0.5~5.0 MPa, in presence of a first catalyst, 2-chloro-5-trifluoromethylpyridine reacts with chlorine gas to obtain 2,3-dichloro-5-trifluoromethylpyridine;

the first catalyst is at least one selected from supported metal chloride, supported zeolite molecular sieve and supported heteropolyacid.

For the supported metal chloride, its active components are at least one selected from $WCl_6$, $MoCl_5$, $FeCl_3$, $AlCl_3$, $CuCl_2$, $ZnCl_2$, $SnCl_4$, and $SbCl_5$, and the load of the active components is 1~50 wt %, For the supported zeolite molecular sieve, its zeolite molecular sieve is at least one selected from ZSM-5, Beta, X, Y, 5A and L type zeolite molecular sieve, and the load of the zeolite molecular sieve is 1~50 wt %.

For the supported heteropolyacid, its heteropolyacid is at least one selected from phosphotungstic acid, silicotungstic acid, phosphomolybdic acid and silicomolybdic acid, and the load of the heteropolyacid is 1~50 wt %.

In the method for preparing 2,3-dichloro-5-trifluoromethylpyridine provided by the present invention, using 2-chloro-5-trifluoromethylpyridine and chlorine gas as the raw material, reacts in presence of the first catalyst, to obtain 2,3-dichloro-5-trifluoromethylpyridine. For the first catalyst used, metal chloride, zeolite molecular sieve or heteropolyacid are supported on a carrier, to provide dispersion of the active components, making it suitable for the reaction for preparing 2,3-dichloro-5-trifluoromethylpyridine using 2-chloro-5-trifluoromethylpyridine and chlorine gas as the raw materials, and the selectivity of the desired compound 2,3-dichloro-5-trifluoromethylpyridine can be significantly increased.

The first catalyst used in the present invention is at least one selected from supported metal chloride, zeolite molecular sieve and heteropolyacid.

When the first catalyst is a supported metal chloride, its active components are at least one selected from $WCl_6$, $MoCl_5$, $FeCl_3$, $AlCl_3$, $CuCl_2$, $ZnCl_2$, $SnCl_4$, and $SbCl_5$.

Preferably, the active components are at least one selected from $WCl_6$, $MoCl_5$, $ZnCl_2$, $FeCl_3$.

In the supported metal chloride, the load of the active component is preferably 1~50 wt %.

Further preferably, the load of the active components is 5~20 wt %.

When the first catalyst is a supported zeolite molecular sieve, the zeolite molecular sieve is at least one selected from ZSM-5, Beta, X, Y, 5A and L type zeolite molecular sieve.

Preferably, the zeolite molecular sieve is at least one selected from ZSM-5, Beta, L.

For the zeolite molecular sieve, its Si/Al ratio may be one that facilitates the reaction. Preferably, Si/Al ratio of the zeolite molecular sieve is 200 or less, and the counter cation is at least one selected from $H^+$, alkali metal ion, alkaline earth metal ion, transition metal ion and rare earth metal ion.

For the supported zeolite molecular sieve, the load of the zeolite molecular sieve is preferably 1~50 wt %.

Further preferably, the load of the zeolite molecular sieve is 5~20 wt %.

When the first catalyst is a supported heteropolyacid, the heteropolyacid is at least one selected from phosphotungstic acid, silicotungstic acid, phosphomolybdic acid and silicomolybdic acid.

In the supported heteropolyacid, the load of the heteropolyacid is preferably 1~50 wt %.

Further preferably, the load of the heteropolyacid is 5~20 wt %.

The carrier used in the first catalyst according to the present invention is preferably at least one selected from silicon dioxide, alumina, titania, zirconia, activated carbon, silicon carbide and mesoporous molecular sieve.

For the method for preparing 2,3-dichloro-5-trifluoromethylpyridine provided by the present invention, the amount of the catalyst may be one that facilitates the reaction.

Preferably, the amount of the first catalyst is 0.1~30 wt % of the mass of 2-chloro-5-trifluoromethylpyridine.

Further preferably, the amount of the first catalyst is 5~20 wt % of the mass of 2-chloro-5-trifluoromethylpyridine.

In the method for preparing 2,3-dichloro-5-trifluoromethylpyridine provided by the present invention, the ratio of raw material chlorine gas to 2-chloro-5-trifluoromethylpyridine may be one that facilitates the reaction.

Preferably, the molar ratio of the chlorine gas to 2-chloro-5-trifluoromethylpyridine is 0.5~10:1.

Further preferably, the molar ratio of the chlorine gas to 2-chloro-5-trifluoromethylpyridine is 1~3:1.

In the method for preparing 2,3-dichloro-5-trifluoromethylpyridine of provide by the present invention, the reaction pressure needs to be one that facilitates the reaction.

Preferably, the reaction pressure is 0.5~5.0 MPa.

Further preferably, the reaction pressure is 1.0~2.0 MPa.

For the method for preparing 2,3-dichloro-5-trifluoromethylpyridine of provided by the present invention provide, the reaction temperature may be one that facilitates the reaction.

Preferably, the reaction temperature is 100~150° C.

For the method for preparing 2,3-dichloro-5-trifluoromethylpyridine provided by the present invention, preferably the reaction is conducted in an autoclave. For the autoclave, its material is preferably selected from 316L, Monel alloy, Inconel alloy or Hastelloy alloy.

For the method for preparing 2,3-dichloro-5-trifluoromethylpyridine provided by the present invention, after the reaction is finished, an alkaline solution can be firstly added, then separated to obtain 2,3-dichloro-5-trifluoromethylpyridine.

the alkaline solution can be an organic base and/or an inorganic base. the organic base is preferably at least one selected from dimethylamine, diethylamine, triethylamine, dipropylamine and tripropylamine. the inorganic base is preferably at least one selected from NaOH, $Na_2CO_3$, $NaHCO_3$, KOH, $K_2CO_3$, $KHCO_3$ and aqueous ammonia.

For 2,3-dichloro-5-trifluoromethylpyridine prepared by the present invention, a qualitative analysis can be conducted by GC-MS, and a quantitative analysis can be conducted by gas chromatography internal standard method.

The calculating formulas for the conversion of 2-chloro-5-trifluoromethylpyridine as well as the selectivity and the yield of the product 2,3-dichloro-5-trifluoromethylpyridine according to the present invention are as follows:

(1) conversion of 2,5-CTF: X2,5-CTF=moles of 2,5-CTF consumed during the reaction/moles of 2,5-CTF added to the reactor×100%;

(2) selectivity of the product i: $S_i$=moles of the product i/moles of 2,5-CTF consumed during the reaction×100%;

(3) yield of the product i: $Y_i = X_{2,5\text{-}CTF} \times S_i$=moles of the product i/moles of 2,5-CTF added to the reaction×100%, Wherein, i represents a product such as 2,3,5-DCTF, 2,6,3-DCTF and 2,3,6,5-TCTF etc.

Compared to the prior art, the method for preparing 2,3-dichloro-5-trifluoromethylpyridine provided by the present invention has the advantages as follows: high selectivity and yield of the desired product 2,3-dichloro-5-trifluoromethylpyridine, and they can reach 90% or more; small catalyst amount, and easy to separate with the reactants, it can realize recycling of the catalyst; without need to use an organic solvent, low cost, and high utilization efficiency of chlorine gas.

Further, in order to reduce unit consumption, to reduce separation cost, and to improve safety, the present invention also provides the following method for preparing 2-chloro-5-trifluoromethylpyridine.

A method for preparing 2-chloro-5-trifluoromethylpyridine, the method is a two-stage method, comprising:

(1) chlorofluorination reaction: in presence of a chlorofluorination catalyst, the chlorofluorination temperature is maintained at 150~320° C., 3-methylpyridine, chlorine gas and hydrogen fluoride are introduced into the chlorofluorination reaction region, to obtain a mixed gas comprising 3-trifluoromethylpyridine;

(2) chlorination reaction: in presence of the chlorination catalyst, the chlorination temperature is maintained at 220~380° C., the mixed gas comprising 3-trifluoromethylpyridine obtained in step (1) is introduced into the chlorination reaction region, to obtain 2-chloro-5-trifluoromethylpyridine, the chlorination catalyst is selected from fluoride, oxide, hydroxide, carbonate or chloride of magnesium, calcium, barium, a palladium catalyst supported on activated carbon, alumina or aluminium fluoride.

The above-mentioned preparing method provided by the present invention is a two-stage method reaction, comprising chlorofluorination reaction step and chlorination reaction step. Wherein, in the chlorofluorination reaction step, it is required to use a chlorofluorination catalyst.

the chlorofluorination catalyst can be a common chlorofluorination catalyst in the art.

As a preferred embodiment, the chlorofluorination catalyst includes a main catalyst, a first co-catalyst and a second co-catalyst; the main catalyst is at least one selected from aluminium, magnesium and chromium, the first co-catalyst is at least one selected from iron, cobalt, manganese, nickel, copper, bismuth and zinc, and the second co-catalyst is at least one selected from lanthanum, cerium, barium, calcium, sodium and potassium.

As a further preferred embodiment, in the chlorofluorination catalyst, the main catalyst is selected from aluminium and/or chromium, the first co-catalyst is at least one selected from iron, nickel and copper, and the second co-catalyst is at least one selected from lanthanium, barium and calcium.

In the chlorofluorination catalyst, the ratio among the main catalyst, the first co-catalyst and the second co-catalyst may be one that facilitates the reaction.

Preferably, the molar ratio among the main catalyst, the first co-catalyst and the second co-catalyst is 50~95:5~42:0.3~8.

Further preferably, the molar ratio among the main catalyst, the first co-catalyst and the second co-catalyst is 75~90:10~20:1~5.

For the preparing method provided by the present invention, in step (1) of chlorofluorination reaction step, the ratio among the raw material 3-methylpyridine, chlorine gas and hydrogen fluoride may be one that facilitates the reaction.

Preferably, the molar ratio among the 3-methylpyridine, chlorine gas and hydrogen fluoride is 1:0.1~50:1~30.

Further preferably, the molar ratio of among the 3-methylpyridine, chlorine gas and hydrogen fluoride is 1:4~10:3~12.

Wherein, the raw material 3-methylpyridine can be directly added to the reaction in a form of gas, and it also can be added to the reaction in a form of mixed gas after inert gas dilution.

Preferably, the 3-methylpyridine is a mixed gas after inert gas dilution.

Wherein, the proportion of 3-methylpyridine in the mixed gas after inert gas dilution may be one that facilitates the reaction.

Preferably, the molar ratio of the 3-methylpyridine to the mixed gas is 1:0.5~50.

Further preferably, the molar ratio of the 3-methylpyridine to the mixed gas is 1:5~20.

For the preparing method provided by the present invention, in step (1) of chlorofluorination reaction, the contact time of the raw material 3-methylpyridine, chlorine gas and hydrogen fluoride with the chlorofluorination catalyst may be one that facilitates the reaction.

Preferably; the contact time of the 3-methylpyridine, chlorine gas and hydrogen fluoride with the chlorofluorination catalyst is 0.5~40 s.

Further preferably, the contact time of the 3-methylpyridine, chlorine gas and hydrogen fluoride with the chlorofluorination catalyst is 1.5~20 s.

For the preparing method provided by the present invention, in step (2) of chlorination reaction, the chlorination catalyst used is selected from fluoride, oxide, hydroxide, carbonate or chloride of magnesium, calcium, barium, a palladium catalyst supported on activated carbon, alumina or aluminium fluoride.

the fluoride, oxide, hydroxide, carbonate and chloride of magnesium, calcium, barium can be magnesium fluoride, calcium fluoride, barium fluoride, magnesium oxide, calcium oxide, barium oxide, magnesium hydroxide, calcium hydroxide, barium hydroxide, magnesium carbonate, calcium carbonate, barium carbonate, magnesium chloride, calcium chloride, and barium chloride.

the supported palladium catalyst being supported on activated carbon, alumina or aluminium fluoride can be a supported palladium catalyst being supported on activated carbon, a supported palladium catalyst being supported on alumina, a supported palladium catalyst being supported on aluminium fluoride.

Preferably, the chlorination catalyst is selected from fluoride, oxide or chloride of magnesium, calcium, a supported palladium catalyst being supported on activated carbon or aluminium fluoride.

For the preparing method provided by the present invention, in step (2) of chlorination reaction, the contact time of the mixed gas comprising 3-trifluoromethylpyridine with the chlorination catalyst may be one that facilitates the reaction.

Preferably, the contact time of the mixed gas comprising 3-trifluoromethylpyridine with the chlorination catalyst is 0.5~40 s.

Further preferably, the contact time of the mixed gas comprising 3-trifluoromethylpyridine with the chlorination catalyst is 1.5~20 s.

The preparing method provided by the present invention is a two-stage type method, comprising chlorofluorination reaction step and chlorination reaction step, a temperature control between the two steps has an influence on the reaction results.

Preferably, the chlorofluorination temperature is 150~320° C., and the chlorination temperature is 220~380° C.

Further preferably, the chlorofluorination temperature is 220~260° C., and the chlorination temperature is 270~320° C.

The preparing method provided by the present invention is preferably conducted in a fixed bed or fluidized bed reactor.

For the preparing method provided by the present invention, calculating formulas of the yield of each compounds are as follows:

Yield of product $i$: $Y_i=(m_i/M_i)/(m_{3\text{-}MP}/M_{3\text{-}MP})\times 100\%$, Yield of other products: $Y_{other}=(1-\Sigma Y_i)\times 100\%$, Wherein i represents four substances such as 3-TF, 2,5-CTF, 2,3-CTF, 2,6,3-DCTF etc., the other products include the by-products in which methyl group on side chain is insufficiently chlorofluorinated and the ring is excessively chlorinated, and substances lost in the experimental procedure. Since under the given reaction condition, in each following examples the conversions of 3-methylpyridine are all 100%, in the present invention the yield of the product i is the selectivity of the product i.

Compared to the previous method, The above preparing method of 2-chloro-5-trifluoromethylpyridine has advantages as follows: improving the selectivity and the yield of the desired product 2-chloro-5-trifluoromethylpyridine by designing and using chlorofluorination catalyst and chlorination catalyst, the selectivity and the yield of 2-chloro-5-trifluoromethylpyridine are up to 76.7%; the gas from the first stage reaction region directly enters into the second stage reaction region for reaction, without operations of cooling, separation, and revaporization, the operation is simple, the energy consumption is reduced; by the two-stage type reaction, the temperature of each stage reaction is low, and the content of the by-products is small.

The present invention also provides the following method for preparing 2-chloro-5-trifluoromethylpyridine, it has characteristics such as high raw material conversion, high selectivity of desired product, low reaction temperature, low energy consumption, easy to separate, without use of organic solvent, initiator and photochlorination reactor.

For the method for preparing 2-chloro-5-trifluoromethylpyridine provided by the present invention, its chemical reaction formula is as follow:

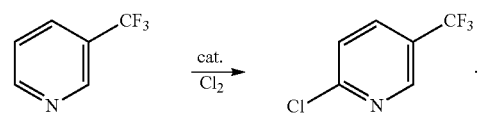 [SMILES: FC(F)(F)c1cccnc1 ; "Cl2" ; FC(F)(F)c1ccc(Cl)nc1]

The present invention provides a technical solution as follow:

A method for preparing 2-chloro-5-trifluoromethylpyridine, the method comprises:

in presence of a second catalyst, the reaction temperature is maintained at 150~350° C., and 3-trifluoromethylpyridine reacts with chlorine gas in the gas phase, to obtain 2-chloro-5-trifluoromethylpyridine;

the second catalyst is at least one selected from ZSM-5, 5A, β and 13× molecular sieve, for the ZSM-5 molecular sieve, its Si/Al is 50~300, the counter cation is at least one selected from $H^+$, $Na^+$, $K^+$, $Ca^{2+}$.

For the preparing method provided by the present invention, the catalyst used is at least one selected from ZSM-5, 5A, β and 13× molecular sieve.

When the second catalyst is the ZSM-5 molecular sieve, as a preferred embodiment, its SiIAl ratio is 50~300, the counter cation is at least one selected from $H^+$, $Na^+$, $K^+$, $Ca^{2+}$.

As a further preferred embodiment, for the ZSM-5 molecular sieve, its Si/Al ratio is 80~200, the counter cation is at least one selected from $H^+$, $Na^+$ and $K^+$.

For the preparing method provided by the present invention, the reaction temperature may be one that facilitates the reaction.

Preferably, the reaction temperature is 150~350° C.

Further preferably, the reaction temperature is 200~300° C.

For the preparing method provided by the present invention provide, the molar ratio of 3-trifluoromethylpyridine to chlorine gas may be one that facilitates the reaction.

Preferably, the molar ratio of the 3-trifluoromethylpyridine to chlorine gas is 1:0.1~20.

Further preferably, the molar ratio of the 3-trifluoromethylpyridine to chlorine gas is 1:0.5~5.

For the preparing method provided by the present invention, the contact time of 3-trifluoromethylpyridine with chlorine gas within the catalyst bed may be one that facilitates the reaction.

Preferably, the contact time of the 3-trifluoromethylpyridine with chlorine gas within the catalyst bed is 0.5~100 s.

Further preferably, the contact time of the 3-trifluoromethylpyridine with chlorine gas within the catalyst bed is 15~70 s.

For the preparing method provided by the present invention, the reaction can be conducted in the fixed bed or fluidized bed reactor.

Preferably, the reaction is conducted in the fluidized bed reactor.

The material of the reactor may be quartz tube and Inconel alloy, etc.

Compared to the previous method, the above method for preparing 2-chloro-5-trifluoromethylpyridine has the following advantages: high selectivity of the desired product 2-chloro-5-trifluoromethylpyridine, high atom utilization; direct feed of raw material 3-trifluoromethylpyridine, without need to use an organic diluent, without need of vaporization and separation on the diluent; low reaction temperature, small energy consumption.

The present invention also provides a method for preparing 2-chloro-5-trifluoromethylpyridine, it has characteristics such as high conversion of raw material, high desired product selectivity, low reaction temperature, low energy consumption, easy to separate, and without need to use organic solvent, initiator and photochlorination reactor.

For the method for preparing 2-chloro-5-trifluoromethylpyridine provided by the present invention, its chemical reaction formula is as follow:

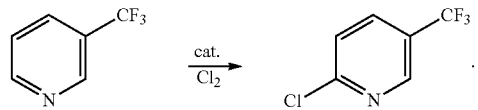 [SMILES: FC(F)(F)c1cccnc1 ; "Cl2" ; FC(F)(F)c1ccc(Cl)nc1]

The present invention provides a technical solution as follow:

A method for preparing 2-chloro-5-trifluoromethylpyridine, the method comprises:

In presence of a third catalyst, the reaction temperature is maintained at 220~360° C., 3-trifluoromethylpyridine and chlorine gas are passed through a catalyst bed, to obtain 2-chloro-5-trifluoromethylpyridine;

the third catalyst is selected from fluoride, oxide, hydroxide carbonate or chloride of magnesium, calcium, barium, a supported palladium catalyst being supported on activated carbon, alumina or aluminium fluoride.

For the preparing method provided by the present invention, the third catalyst used is selected from fluoride, oxide, hydroxide, carbonate or chloride of magnesium, calcium, barium, a supported palladium catalyst being supported on activated carbon, alumina or aluminium fluoride.

the fluoride, oxide, hydroxide, carbonate and chloride of magnesium, calcium, barium can be magnesium fluoride, calcium fluoride, barium fluoride, magnesium oxide, calcium oxide, barium oxide, magnesium hydroxide, calcium hydroxide, barium hydroxide, magnesium carbonate, calcium carbonate, barium carbonate, magnesium chloride, calcium chloride, barium chloride.

the supported palladium catalyst being supported on activated carbon, alumina or aluminium fluoride can be a supported palladium catalyst being supported on activated carbon, a supported palladium catalyst being supported on alumina, a supported palladium catalyst being supported on aluminium fluoride.

As a preferred embodiment, the third catalyst is selected from fluoride, oxide or chloride of magnesium, calcium, a palladium catalyst being supported on activated carbon or aluminium fluoride.

When the third catalyst used is the supported palladium catalyst being supported on activated carbon, alumina or aluminium fluoride, the mass percentage of in the catalyst may be one that facilitates the reaction.

Preferably, the mass percentage of the palladium in the catalyst is 0.1~10 wt %.

Further preferably, the mass percentage of the palladium in the catalyst is 0.5~3 wt %.

When the third catalyst used is the supported palladium catalyst being supported on activated carbon, alumina or aluminium fluoride, as a preferred embodiment, an activating pretreatment is conducted before use.

the activating pretreatment can be an activating pretreatment against the supported palladium catalyst by using nitrogen gas and/or chlorine gas at a temperature of 120~350° C.

For the preparing method provided by the present invention, the reaction temperature may be one that facilitates the reaction.

Preferably, the reaction temperature is 220~360° C.

Further preferably, the reaction temperature is 270~320° C.

For the preparing method provided by the present invention, the molar ratio of 3-trifluoromethylpyridine to chlorine gas may be one that facilitates the reaction.

Preferably, the molar ratio of the 3-trifluoromethylpyridine to chlorine gas is 1:0.1~50.

Further preferably, the molar ratio of the 3-trifluoromethylpyridine to chlorine gas is 1:4~10.

For the preparing method provided by the present invention, the contact time of 3-trifluoromethylpyridine with chlorine gas within the catalyst bed may be one that facilitates the reaction.

Preferably, the contact time of the 3-trifluoromethylpyridine with chlorine gas within the catalyst bed is 1~60 s.

Further preferably, the contact time of the 3-trifluoromethylpyridine with the chlorine gas within the catalyst bed is 5~30 s.

For the preparing method provided by the present invention, the reaction can be conducted in a fixed bed or fluidized bed reactor.

Preferably, the reaction is conducted in the fluidized bed reactor.

For the preparing method provided by the present invention, the product obtained is washed with water and alkaline solution and distilled, to obtain an oily product, i.e. 2-chloro-5-trifluoromethylpyridine.

Since under the given reaction condition, the conversion of 3-trifluoromethylpyridine in the following examples are all 100%, in the present invention the yield of the desired product is the selectivity of the desired product.

Compared to the previous method for preparing 2-chloro-5-trifluoromethylpyridine, the above method has the following advantages: high selectivity of the desired product 2-chloro-5-trifluoromethylpyridine, high atom utilization; direct feed of raw material 3-trifluoromethylpyridine, without need to use an organic diluent, without need to conduct additional vaporization and separation against the diluent; low reaction temperature, and small energy consumption.

DETAILED DESCRIPTION

The present invention will be further described below in conjunction with the specific examples, but the present invention is not restricted by these specific examples. Those skilled in the art should recognize that, the present invention covers all alternatives, improvements and equivalent that may be included in the claims.

Example 1

2-chloro-5-trifluoromethylpyridine (90.8 g, 0.5 mol) and 15% $WCl_6$/AC ($WCl_6$ supported on activated carbon, the load was 15 wt %, 12 g) were added into a 250 mL autoclave (Inconel alloy), after the kettle cover was installed, a nitrogen gas of 2 MPa was charged and the pressure was maintained for 2 h, a leakage detection was conducted to the reaction kettle, after the reaction kettle was confirmed to be gastight, it was placed into an ice ethanol bath for cooling, when the reaction kettle was cooled to 0° C., about 37.5 g of chlorine gas (0.5 mol) was charged into the reaction kettle from the reaction kettle gas phase tube, then the reaction kettle was placed into a heating jacket with a magnetic stirrer, under a stirring condition the reaction system was heated to 150° C., at this time the pressure of the reaction system was about 2.0 MPa, at this temperature continuously reacted for 20 h. After the reaction was finished, when the temperature of the reaction system dropped to room temperature, nitrogen gas was charged into the reaction kettle from a liquid phase tube and a replacement was conducted for 30 min (the tail gas being replaced out was introduced into a alkaline washing bottle for absorption, and neutralized), the reaction kettle was opened, the catalyst and the products were separated by filtration, and a 10 wt % of NaOH solution was added to the products for neutralization, extracted, and liquid separated, to obtain an oily product. The oily product obtained was dried on anhydrous sodium sulfate then weighed and the mass was 107.0 g, a qualitative analysis was conducted by GC-MS, and a quantitative analysis was conducted by gas chromatography internal standard method. The conversion of 2-chloro-5-trifluoromethylpyridine as well as the selectivity and the yield of the chlorination reaction product are seen in Table 1.

Example 2

The reaction temperature in Example 1 dropped from 150° C. to 100° C., other reaction condition and product treatment method were same as Example 1. The mass of the finally obtained oily product after drying was 91.2 g. The conversion of 2-chloro-5-trifluoromethylpyridine as well as the selectivity and the yield of the chlorination reaction products are seen Table 1.

Example 3

15% $WCl_6$/AC ($WCl_6$ supported on activated carbon, the load was 15 wt %, 12 g) in Example 1 was changed to 15% $MoCl_5$/AC ($MoCl_5$ supported on activated carbon, the load was 15 wt %, 12 g), other reaction condition and product treatment method were same as Example 1. The mass of the finally obtained oily product after drying was 97.9 g. The conversion of 2-chloro-5-trifluoromethylpyridine as well as the selectivity and the yield of the chlorination reaction product are seen in Table 1.

Example 4

15% $WCl_6$/AC ($WCl_6$ supported on activated carbon, the load was 15 wt %, 12 g) in Example 1 was changed to 15% $FeCl_3$/AC ($FeCl_3$ supported on activated carbon, the load was 15 wt %, 12 g), other reaction condition and the product treatment method were same as Example 1. The mass of the finally obtained oily product after drying was 107.2 g. The conversion of 2-chloro-5-trifluoromethylpyridine as well as the selectivity and the yield of the chlorination reaction product are seen Table 1.

Example 5

15% $WCl_6$/AC ($WCl_6$ supported on activated carbon, the load was 15 wt %, 12 g) in Example 1 was changed to 15% $CuCl_2$/AC ($CuCl_2$ supported on activated carbon, the load was 15 wt %, 12 g), other reaction condition and the product treatment method were same as Example 1. The mass of the oily product finally obtained after drying was 100.9 g. The conversion of 2-chloro-5-trifluoromethylpyridine as well as the selectivity and the yield of the chlorination reaction products are seen in Table 1.

Example 6

15% $WCl_6$/AC ($WCl_6$ supported on activated carbon, the load was 5 wt %, 12 g) in Example 1 was changed to 15% CuCl/AC ($CuCl_2$ supported on activated carbon, the load was 15 wt %, 12 g), other reaction condition and the product treatment method were same as Example 1. The mass of the finally obtained oily product after drying was 98.1 g. The conversion of 2-chloro-5-trifluoromethylpyridine as well as the selectivity and the yield of the chlorination reaction products are seen in Table 1.

Example 7

15% $WCl_6$/AC ($WCl_6$ supported on activated carbon, the load was 15 wt %, 12 g) in Example 1 was changed to 15% $ZnCl_2$/AC ($ZnCl_2$ supported on activated carbon, the load was 15 wt %, 12 g), other reaction condition and the product treatment method were same as Example 1. The mass of the finally obtained oily product after drying was 100.7 g. The conversion of 2-chloro-5-trifluoromethylpyridine as well as the selectivity and the yield of chlorination reaction product are seen in Table 1.

Example 8

15% $WCl_6$/AC ($WCl_6$ supported on activated carbon, the load was 15 wt %, 12 g) in Example 1 was changed to 15% $AlCl_3$/AC ($AlCl_3$ supported on activated carbon, the load was 15 wt %, 12 g), other reaction condition and the product treatment method were same as Example 1. The mass of the finally obtained oily product after drying was 105.2 g. The conversion of 2-chloro-5-trifluoromethylpyridine as well as the selectivity and the yield of the chlorination reaction product are seen in Table 1.

Example 9

15% $WCl_6$/AC ($WCl_6$ supported on activated carbon, the load was 15 wt %, 12 g) in Example 1 was changed to 15 wt % NaY/AC (NaY zeolite molecular sieve supported on activated carbon, the load was 15 wt %, Si/Al of NaY=5.4, 12 g), other reaction condition and the product treatment method were same as Example 1. The mass of finally obtained oily product after drying was 103.5 g. The conversion of 2-chloro-5-trifluoromethylpyridineas well as the selectivity and the yield of the chlorination reaction products are seen in Table 1.

Example 10

15% $WCl_6$/AC ($WCl_6$ supported on activated carbon, the load was 15 wt %, 12 g) in Example 1 was changed to 15% HPW/AC (phosphotungstic acid supported on activated carbon, the load was 15 wt %, 12 g), other reaction condition and the product treatment method were same as Example 1. The mass of the finally obtained oily product after drying was 106.8 g. The conversion of 2-chloro-5-trifluoromethylpyridine as well as the selectivity and the yield of the chlorination reaction product are seen in Table 1.

Example 11

15% $WCl_6$/AC ($WCl_6$ supported on activated carbon, the load was 15 wt %, 12 g) in Example 1 was changed to 15% HSiW/AC (silicotungstic acid supported on activated carbon, the load was 15 wt %, 12 g), other reaction condition and the product treatment method were same as Example 1. The mass of the finally obtained oily product after drying was 93.2 g. The conversion of 2-chloro-5-trifluoromethylpyridine as well as the selectivity and the yield of the chlorination reaction product are seen in Table 1.

Example 12

15% $WCl_6$/AC ($WCl_6$ supported on activated carbon, the load was 15 wt %, 12 g) in Example 1 was changed to 15% $HPW/TiO_2$ (phosphotungstic acid supported on $TiO_2$, the load was 15 wt %, 12 g), other reaction condition and the product treatment method were same as Example 1. The mass of the finally obtained oily product after drying was 93.2 g. The conversion of 2-chloro-5-trifluoromethylpyridine as well as the selectivity and the yield of the chlorination reaction product are seen in Table 1.

Example 13

The introducing amount of chlorine gas in Example 1 was increased from 35.5 g (0.5 mol) to 71.0 g (1.0 mol), other reaction condition and the product treatment method were same as Example 1. The mass of the finally obtained oily product after drying was 108.7 g. The conversion of 2-chloro-5-trifluoromethylpyridine as well as the selectivity and the yield of the chlorination reaction product are seen in Table 1.

Comparative Example 1

15% $WCl_6$/AC ($WCl_6$ supported on activated carbon, the load was 15 wt %, 12 g) in Example 1 was changed to $WCl_6$ (non-supported, 1.8 g), other reaction conditions and the product treatment method were same as Example 1. The mass of finally obtained oily product after drying was 98.2 g. The conversion of 2-chloro-5-trifluoromethylpyridine as well as the selectivity and the yield of the chlorination reaction product are seen in Table 1. Compared to Example 1, it is known that when the active component was not supported on AC, not only the conversion of 2-chloro-5-trifluoromethylpyridine was decreased from 99.9% to 65.2%, but also the selectivity of the desired product 2,3-dichloro-5-trifluoromethylpyridine was significantly reduced from 92.1% to 65.7%. It is seen that supporting the metal chloride on a carrier with high specific surface area can significantly improve its catalytic performance.

Comparative Example 2

The reaction temperature in Example 1 was raised from 150° C. to 200° C., other reaction condition and the product treatment method were same as Example 1. The mass of the finally obtained oily product after drying was 109.5 g. The conversion of 2-chloro-5-trifluoromethylpyridine as well as the selectivity and the yield of chlorination reaction product are seen in Table 1.

TABLE 1

| Example | conversion of 2,5-CTF % | selectivity % | | | |
|---|---|---|---|---|---|
| | | 2,3,5-DCTF | 2,6,3-DCTF | 2,3,6,5-TCTF | other |
| 1 | 99.9 | 92.1 | 4.6 | 1.2 | 2.1 |
| 2 | 10.2 | 88.2 | 1.2 | 0.5 | 10.1 |
| 3 | 40.5 | 90.3 | 3.0 | 1.3 | 5.4 |
| 4 | 92.9 | 87.1 | 8.4 | 1.8 | 2.7 |
| 5 | 56.2 | 82.7 | 0.6 | 4.9 | 11.8 |
| 6 | 53.2 | 85.9 | 3.0 | 1.3 | 6.3 |
| 7 | 65.5 | 90.4 | 1.6 | 1.6 | 6.5 |
| 8 | 79.9 | 85.9 | 7.1 | 1.9 | 5.1 |
| 9 | 55.3 | 88.6 | 5.2 | 0.7 | 2.4 |

TABLE 1-continued

| Example | conversion of 2,5-CTF % | selectivity % | | | |
|---|---|---|---|---|---|
| | | 2,3,5-DCTF | 2,6,3-DCTF | 2,3,6,5-TCTF | other |
| 10 | 98.7 | 90.6 | 0 | 2.3 | 7.0 |
| 11 | 39.9 | 94.9 | 0 | 0.9 | 4.2 |
| 12 | 19.8 | 86.4 | 9.1 | 0.8 | 3.7 |
| 13 | 100.0 | 91.2 | 3.2 | 2.5 | 3.1 |
| Comparative Example 1 | 65.2 | 65.7 | 5.2 | 2.1 | 7.0 |
| Comparative Example 2 | 100.0 | 60.2 | 10.3 | 23.0 | 6.5 |

Example 14

The internal diameter of the heating furnace was 30 mm, and the height was 600 mm, the upper and lower two stages were respectively temperature controlled. The upper stage was the chlorofluorination reaction region, and the lower stage was the chlorination reaction region. The internal diameter of the reaction tube was 19 mm, the length was 700 mm, and the material was stainless steel, the catalyst loading heights in the upper and lower two-stage were all 140 mm, and ensuring that the catalyst beds in the upper and the lower two stages were respectively in a constant temperature zone of the upper and lower two-stage heating furnace. The chlorofluorination catalyst bed was composed of 55.5% $MgF_2$-40.0% $Co_2O_3$-0.55% $CeO_2$ (55.5%, 40%, 0.5% are mole percentage of the metal atoms, they are the ratio of metal atom moles of each component to sum of moles of the metal atoms, the composition of the chlorofluorination catalyst was shown as the molar ratio of metal atoms, the same below) of catalyst. The catalyst was molded into a cylinder having a diameter of 3 mm and a height of 4 mm. The chlorination catalyst bed was composed of 1% Pd/activated carbon (1% being the mass ratio of metal palladium in the catalyst after calcination, the compositions of the supported chlorination catalyst are shown as the ratio of the mass of metal atom to the total mass of the catalyst, the same below) of catalyst, the catalyst was molded into a cylinder having a diameter of 3 mm and a height of 4 mm.

The chlorofluorination reaction region was heated to 235° C., and the chlorination reaction region was heated to 290° C. The feed rate of anhydrous hydrogen fluoride was controlled at 10.00 g/h (0.500 mol/h), the catalyst was activated by introducing HF for 3 h, then the 3-methylpyridine being vaporized by using nitrogen gas as the carrier gas and chlorine gas were introduced into the reaction tube. Wherein, the flowrate of 3-methylpyridine was controlled at 4.000 (0.043 mol/h), the flowrate of chlorine gas was controlled at 7.7 L/h (0.344 mol/h), the flowrate of nitrogen gas was maintained at 12.0 L/h (0.536 mol/h). The molar feed ratio of the reactants was 3-methylpyridine:chlorine gas:hydrogen fluoride:nitrogen gas=1:8:11.6:12.5. The contact time of all starting reaction material with the chlorofluorination catalyst bed and the chlorination catalyst bed catalyst were all 4.5 s, and reacted for 8 h.

The tail gas leaving the reaction tube was introduced into water a washing tower and an alkaline washing tower for condensation. The oil layer obtained was separated then neutralized with aqueous ammonia, and a steam distillation was conducted to obtain an oily product. The oily product obtained was dried on anhydrous sodium sulfate then weighed and the mass was 63.04 g, a quantitative analysis was conducted by gas chromatography internal standard method, and the mass content of 2,5-CTF was 70.8%, and the reaction yield was 71.5% (calculated on basis of 3-MP, the same below).

Example 15 the upper stage in the reaction tube in Example 1 was filled with 55.5% $MgF_2$-40% ZnO-0.5% $K_2O$ catalyst, the catalyst was molded into a cylinder having a diameter of 3 mm and a height of 4 mm, the lower stage is filled with 2% Pd/activated carbon catalyst, the catalyst was molded into a cylinder having a diameter of 3 mm and a height of 4 mm.

The chlorofluorination reaction region was heated to 265° C., and the chlorination reaction region was heated to 320° C. The feed rate of anhydrous hydrogen fluoride was 10.00 g/h (0.500 mol/h), the catalyst was activated by introducing HF for 3 h, then 3-methylpyridine being vaporized by using nitrogen gas as the carrier gas and chlorine gas were introduced into the reaction tube. Wherein, the flowrate of 3-methylpyridine was controlled at 4.00 g/h (0.043 mol/h), the flowrate of chlorine gas was controlled at 7.7 L/h (0.344 mol/h), the flowrate of nitrogen gas was maintained at 12.0 L/h (0.536 mol/h). The molar feed ratio of the reactants was 3-methylpyridine:chlorine gas:hydrogen fluoride:nitrogen gas=1:8:11.6:12.5, the contact time of all starting reaction material with the chlorofluorination catalyst bed and the chlorination catalyst bed catalyst were all 4.5 s, and reacted for 8 h.

The treatment method of the tail gas leaving the reaction was same as Example 1. 64.35 g of oily product was obtained, and a gas chromatography analysis was conducted, the mass content of 2,5-CTF was 65.7%, and the reaction yield was 67.8%.

Example 16 the upper stage in the reaction tube in Example 14 was filled with 77.0% $MgF_2$-20.0% $Bi_2O_3$-2.0% $Na_2O$ catalyst, the catalyst was molded into a cylinder having a diameter of 3 mm and a height of 4 mm, the lower stage was filled with $MgF_2$ catalyst, the catalyst was molded into a cylinder having a diameter of 3 mm and a height of 4 mm.

The chlorofluorination reaction region was heated to 220° C., and the chlorination reaction region was heated to 280° C. The feed rate of anhydrous hydrogen fluoride was controlled at 10.00 g/h (0.500 mol/h), the catalyst was activated by introducing HF for 3 h, then 3-methylpyridine being vaporized by using nitrogen gas as the carrier gas and chlorine gas were introduced into the reaction tube. Wherein, the flowrate of 3-methylpyridine was controlled at 4.00 g/h (0.043 mol/h), the flowrate of chlorine gas was controlled at 7.7 L/h (0.344 mol/h), the flowrate of nitrogen gas was maintained at 12.0 L/h (0.536 mol/h). Molar feed ratio of the reactants was 3-methylpyridine:chlorine gas:hydrogen fluoride:nitrogen gas=1:8:11.6:12.5, the contact time of all starting reaction material with the chlorofluorination catalyst bed and chlorination catalyst bed catalyst were all 4.5 s, and reacted for 8 h.

The treatment method of the tail gas leaving the reaction tube was same as Example 14. 61.94 g of oily product was obtained, and gas chromatography analysis was conducted, the mass content of 2,5-CTF was 77.2%, and reaction yield was 76.7%.

Example 17 the upper stage of the reaction tube in Example 14 was filled with 85.0% $CrF_3$-10.0% CuO-5.0% $La_2O_3$ catalyst, the catalyst was molded into a cylinder having a diameter of 3 mm and a height of 4 mm, the lower stage was filled with MgO catalyst, the catalyst was molded into a cylinder having a diameter of 3 mm and a height of 4 mm.

The chlorofluorination reaction region was heated to 235° C., and the chlorination reaction region was heated to 300° C. The feed rate of anhydrous hydrogen fluoride was controlled at 10.32 g/h (0.516 mol/h), the catalyst was activated by introducing HF for 3 h, then 3-methylpyridine and chlorine gas being vaporized by using nitrogen gas as the carrier gas and chlorine gas were introduced into the reaction tube. Wherein, the flowrate of 3-methylpyridine was controlled at 4.00 g/h (0.043 mol/h), the flowrate of chlorine gas was controlled at 8.7 L/h (0.387 mol/h), the flowrate of nitrogen gas was maintained at 12.0 L/h (0.536 mol/h). Molar feed ratio of the reactants was 3-methylpyridine:chlorine gas:hydrogen fluoride:nitrogen gas=1:9:12:12.5, the contact time of all starting reaction material with the chlorofluorination catalyst bed and chlorination catalyst bed catalyst were all 4.0 s, and reacted for 6 h.

The treatment method of the tail gas leaving the reaction tube was same as Example 1. 40.50 g of oily product was obtained, and a gas chromatography analysis was conducted, the mass content of 2,5-CTF was 69.7%, the reaction yield was 74.5%.

Example 18-20

Except for the catalyst, all operation condition was same as Example 16. In Example 18, the upper stage in the reaction tube was filled with 90.0% $CrF_3$-8.0% $Fe_2O_3$-2.0% $La_2O_3$ catalyst, the lower stage was filled with $BaCl_2$ catalyst; in Example 19, the upper stage in the reaction tube was filled with 90.0% $AlF_3$-8.0% NiO-2.0% BaO catalyst, the lower stage was filled with $CaCl_2$ catalyst; in Example 20, the upper stage in the reaction tube was filled with 90.0% $CrF_3$-8.0% NiO-2.0% $Na_2O$ catalyst, the lower stage was filled with 1.5% Pd/activated carbon catalyst.

The reaction respectively obtained 64.30 g, 65.34 g, 64.80 g of oily products, and gas chromatography analysis were conduct, the mass content of 2,5-CTF were respectively 73.2%, 69.9%, 73.3%, the reaction yield were respectively 75.5%, 73.2%, 76.1%.

Example 21

The internal diameter of the heating furnace was 35 mm, and the height was 500 mm, the upper and lower two stages were respectively temperature controlled. The lower stage was chlorofluorination reaction region, and the upper stage was chlorination reaction the region. The material of the reaction tube was Inconel alloy, the internal diameter of the reaction tube was 30 mm, the length was 600 mm. The lower stage of the reaction tube was filled with 60 mL of 85% $AlF_3$-10% $Mn_2O_3$-5% BaO (mean diameter being 0.15 mm) chlorofluorination catalyst, the height of the static bed was 89 mm, the upper stage of the reaction tube was filled with 60 mL of 1% Pd/activated carbon (mean diameter being 0.15 mm) chlorination catalyst, the height of the static bed was 89 mm. Distribution plates were placed at bottom of the reactor and middle of the reactor, for distribution of the gas flow and isolation and support of the catalyst. After 1 h of fluidization with nitrogen gas at 235° C. HF was charged at a feed rate of 8.59 g/h (0.430 mol/h) for 4 h, fluorination was conducted to the catalyst. Then, 3-methylpyridine being vaporized by using nitrogen gas as the carrier gas and chlorine gas were introduced into the reaction tube. Wherein, the flowrate of 3-methylpyridine was controlled at 4.00 g/h (0.043 mol/h), the flowrate of chlorine gas was controlled at 5.77 L/h (0.258 mol/h), and the flowrate of nitrogen gas was maintained at 9.6211 h (0.430 mol/h). The molar feed ratio of the reactants was 3-methylpyridine:chlorine gas:hydrogen fluoride:nitrogen gas=1:6:10:10, the contact time of all starting reaction materials with the chlorofluorination catalyst bed and the chlorination catalyst bed catalyst were all 5.5 s, and reacted for 24 h.

The tail gas leaving the reaction tube was introduced into the water washing tower and the alkaline washing tower for condensation. The oil layer obtained was separated then neutralized with aqueous ammonia, and a steam distillation was conducted to obtain an oily product. The oily product obtained was dried on anhydrous sodium sulfate then weighed and the mass was 166.49 g, a quantitative analysis was conducted by gas chromatography internal standard method, the mass content of 2,5-CTF was 67.3%, and the reaction yield was 73.9%.

Example 22

Except that the catalyst was different, other condition was same as Example 21. The lower stage of the reaction tube was filled with 60 mL of 90% $AlF_3$-9% $ZnCl_2$-1% CaO (mean diameter being 0.15 mm) chlorofluorination catalyst, the upper stage was filled with 60 mL of 1% $Pd/Al_2O_3$ (mean diameter being 0.15 mm) chlorination catalyst. The product treatment and the analysis method were same as Example 21, to obtain 158.90 g of an oily product, the mass content of 2,5-CTF was 68.8%, and the reaction yield was 72.1%.

Example 23

A stainless steel tube with a reaction tube internal diameter of 25 mm and length of 800 mm was used as the fixed bed reactor, and HZSM-5 molecular sieve with a volume of 40 mL and a particle size of 5-10 mesh and Si/Al ratio of 100 (which means that $H^+$ is the counter cation) was filled into middle of the fixed bed reactor, a reaction tube line was linked, and nitrogen gas was introduced for purge, the flowrate of nitrogen gas was 100 mL/min. The reaction furnace was heated up to 290° C. at a heating rate of 5° C./min, after the catalyst bed reached the reaction temperature nitrogen gas purge was stopped and changed to introduction of chlorine gas for purge, meanwhile 3-trifluoromethylpyridine was continuously introduced into the fixed bed reactor, to initiate the reaction. The molar ratio of the reaction raw material 3-trifluoromethylpyridine to chlorine gas was 1:2, the contact time of the reactants within the catalyst bed was 30.9 s. The reaction product was condensed by an ice water bath then collected in a collection bottle, to obtain an oily product. After the reaction was finished, water washing and alkaline washing and acid-removal were conducted to the oily product, then dried on anhydrous sodium sulfate and distillation was conducted, a qualitative analysis was conducted to the distillate by GC-MS, a quantitative analysis was conducted to the distillate composition by gas chromatography internal standard method.

After the quantitative analysis, the reaction results were: the conversion of 3-trifluoromethylpyridine was 98.7%, and the selectivity of 2-chloro-5-trifluoromethylpyridine was 93.8%.

Example 24

Except for the catalyst, other condition was same as Example 23, the catalyst used was 5A molecular sieve.

After a quantitative analysis, the reaction results were: the conversion of 3-trifluoromethylpyridine was 89.2%, and the selectivity of 2-chloro-5-trifluoromethylpyridine was 89.0%.

Example 25

Except for the catalyst, other condition was same as Example 23, the catalyst used was 13× molecular sieve.

After a quantitative analysis, the reaction results were: the conversion of 3-trifluoromethylpyridinecon was 91.5%, and the selectivity of 2-chloro-5-trifluoromethylpyridine was 88.3%.

Example 26

Except for the catalyst, other condition was same as Example 23, the catalyst used was β molecular sieve.

After a quantitative analysis, the reaction results were: the conversion of 3-trifluoromethylpyridine was 92.3%, and the selectivity of 2-chloro-5-trifluoromethylpyridine was 89.2%.

Example 27

Except for the reaction temperature, other condition was same as Example 23, the reaction temperature was 350° C.

After a quantitative analysis, the reaction results were: the conversion of 3-trifluoromethylpyridine was 99.9%, and the selectivity of 2-chloro-5-trifluoromethylpyridine was 87.1%.

Example 28

The material of the reaction tube was Inconel alloy, the internal diameter of the reaction tube was 30 mm, the length was 400 mm. The reaction tube was filled with 60 mL of HZSM-5 molecular sieve catalyst with a mean diameter of 0.15 mm and a Si/Al ration of 100, after 1 h of fluidization with nitrogen gas at 235° C., it was heated up to 290° C. at a heating rate of 5° C./min, after the catalyst bed reached the reaction temperature the nitrogen gas purge was stopped and changed to introduction of chlorine gas for purge, meanwhile 3-trifluoromethylpyridine was continuously introduced into the fixed bed reactor, to initiate the reaction. The molar ratio of reaction raw material 3-trifluoromethylpyridine to chlorine gas was 1:2, and the contact time of the reactants within the catalyst bed was 58.5 s. The reaction product was condensed by an ice water bath then collected in a collection bottle, to obtain an oily matter. After the reaction was finished, water washing and alkaline washing and acid-removal were conducted against the oily matter, dried on anhydrous sodium sulfate then distillation was conducted, a qualitative analysis was conducted to the distillate by GC-MS, a quantitative analysis was conducted to the distillate composition by gas chromatography internal standard method.

After the quantitative analysis, the reaction results were: the version of 3-trifluoromethylpyridinecon was 97.9%, and the selectivity of 2-chloro-5-trifluoromethylpyridine was 94.5%.

Example 29

Except for the catalyst, other condition were same as Example 28, the catalyst used was HZSM-5 molecular sieve with Si/Al=50.

After a quantitative analysis, the reaction results were: the conversion of 3-trifluoromethylpyridine was 99.0%, the selectivity of 2-chloro-5-trifluoromethylpyridine was 90.1%.

Example 30

Except for the catalyst, other condition was same as Example 28, the catalyst used was NaZSM-5 (which means $Na^+$ is the counter cation) molecular sieve with Si/Al=100.

After a quantitative analysis, the reaction results were: the conversion of 3-trifluoromethylpyridine was 95.7%, and the selectivity of 2-chloro-5-trifluoromethylpyridine was 92.5%.

Example 31

Except for the catalyst, other condition was same as Example 28, the catalyst used was Si/Al=100 of KZSM-5 (which means $K^+$ is the counter cation) molecular sieve.

After a quantitative analysis, the reaction results were: the conversion of 3-trifluoromethylpyridine was 92.3%, and the selectivity of 2-chloro-5-trifluoromethylpyridine was 92.0%.

Example 32

Except for the catalyst, other condition was same as Example 28, the catalyst used was CaZSM-5 (which means $Ca^{2+}$ is the counter cation) molecular sieve with a Si/Al=100.

After a quantitative analysis, the reaction result were: the conversion of 3-trifluoromethylpyridine was 4.4%, the selectivity of 2-chloro-5-trifluoromethylpyridine was 88.1%.

Example 33

Except for the chlorine gas ratio, other condition was same as Example 23, the molar ratio of raw material 3-trifluoromethylpyridine to chlorine gas was 1:10.

After a quantitative analysis, the reaction results were: the conversion of 3-trifluoromethylpyridine was 98.5%, and the selectivity of 2-chloro-5-trifluoromethylpyridine was 85.2%.

Comparative Example 3

The catalyst in Example 23 was changed to a HZSM-5 molecular sieve with Si/Al of 22, other condition was unchanged.

After a quantitative analysis, the reaction results were: the conversion of 3-trifluoromethylpyridine was 99.9%, but the selectivity of the desired product 2-chloro-5-trifluoromethylpyridine was only 47.3%.

Comparative Example 4

According to the disclosure in China CN104610137 a $FeCl_3$/activated carbon catalyst was used as the catalyst, and the reaction temperature was controlled at 250° C., other operation condition was consistent with Example 23.

After a quantitative analysis, the reaction results were: the conversion of 3-trifluoromethylpyridine was 96.2%, the selectivity of the desired product 2-chloro-5-trifluoromethylpyridine was only 20.2%.

Example 34

The internal diameter of the heating furnace was 30 mm, and the height was 600 mm. The internal diameter of the reaction tube was 19 mm, and the length was 700 mm, the material was stainless steel, the loading height of the catalyst was 140 mm. The catalyst bed was composed of 1% Pd/activated carbon (1% being the mass ratio of metal palladium in the catalyst after calcination, the composition of the supported chlorination catalyst are all shown as the ratio of mass of metal atom to total mass of the catalyst, the same below) catalyst, the catalyst was molded into a cylinder having a diameter of 3 mm and a height of 4 mm. The reaction region was heated to 290° C., the vaporized 3-trifluoromethylpyridine and chlorine gas were introduced into the reaction tube. Wherein, the flowrate of 3-trifluoromethylpyridine was controlled at 6.33 g/h (0.043 mol/h), the flowrate of chlorine gas was controlled at 7.7 L/h (0.344 mol/h). Molar feed ratio of the reactants was 3-trifluoromethylpyridine:chlorine gas=1:8, the contact time of all starting reaction material with the catalyst bed were 16.5 s, and reacted for 8 h.

The tail gas leaving the reaction tube was introduced into the water washing tower and the alkaline washing tower for condensation. The oil layer obtained was separated then neutralized with aqueous ammonia, and a steam distillation was conducted to obtain an oily product. The oily product obtained was dried on anhydrous sodium sulfate then weighed and the mass was 66.28 g, a quantitative analysis was conducted by gas chromatography internal standard method, the mass content of 2-chloro-5-trifluoromethylpyridine was 88.7%, and the yield was 94.1% (calculated relative to 3-trifluoromethylpyridine, the same below).

Example 35 the reaction tube in Example 34 was filled with 2% Pd/activated carbon catalyst, the catalyst was molded into a cylinder having a diameter of 3 mm and a height of 4 mm. The reaction region was heated to 320° C. The vaporized 3-trifluoromethylpyridine and chlorine gas were introduced into the reaction tube. Wherein, the flowrate of 3-trifluoromethylpyridine was controlled at 6.33 g/h (0.043 mol/h), the flowrate of chlorine gas was controlled at 7.7 L/h (0.344 mol/h). Molar feed ratio of the reactants was 3-trifluoromethylpyridine:chlorine gas=1:8, the contact time of all starting reaction materials with the catalyst bed were 16.5 s, and reacted for 8 h.

The treatment method of the tail gas leaving the reaction tube was same as Example 34, to obtain 67.59 g of an oily product, and a gas chromatography analysis was conducted, the mass content of 2-chloro-5-trifluoromethylpyridine was 84.8%, and the yield was 91.7%.

Example 36 the reaction tube in Example 34 was filled with $MgF_2$ catalyst, the catalyst was molded into a cylinder having a diameter of 3 mm and a height of 4 mm. The reaction region was heated to 280° C. The vaporized 3-trifluoromethylpyridine and chlorine gas were introduced into the reaction tube. Wherein, the flowrate of 3-trifluoromethylpyridine was controlled at 6.33 g/h (0.043 mol/h), the flowrate of chlorine gas was controlled at 7.7 L/h (0.344 mol/h). Molar feed ratio of the reactants was 3-trifluoromethylpyridine:chlorine gas=1:8, the contact time of all starting reaction material with the catalyst bed were 16.5 s, and reacted for 8 h.

The treatment method of the tail gas leaving the reaction tube was same as Example 34, to obtain 65.86 g of an oily product, and a gas chromatography analysis was conduct, the mass content of 2-chloro-5-trifluoromethylpyridine of was 87.8%, and the yield was 92.5%.

Example 37 the reaction tube in Example 34 was filled with a MgO catalyst, the catalyst was molded into a cylinder having a diameter of 3 mm and a height of 4 mm. The reaction region was heated to 300° C. The vaporized 3-trifluoromethylpyridine and chlorine gas were introduced into the reaction tube. Wherein, the flowrate of 3-trifluoromethylpyridine was controlled at 6.33 g/h (0.043 mol/h), the flowrate of chlorine gas was controlled at 8.7 L/h (0.387 mol/h). Molar feed ratio of the reactants was 3-trifluoromethylpyridine=1:9, the contact time of all starting reaction material with the catalyst bed were 14.8 s, and reacted for 6 h.

The treatment method of the tail gas leaving the reaction tube was same as Example 34. 48.49 g of an oily product was obtained, and a gas chromatography analysis was conducted, the mass content of 2-chloro-5-trifluoromethylpyridine was 86.7%, and the yield was 89.6%.

Example 38-40

Except for the catalyst, all operation condition was same as Example 35. In Example 38, the reaction tube was filled with $BaCl_2$ catalyst; in Example 39, the reaction tube was filled with $CaCl_2$ catalyst; in Example 40, the reaction tube was filled with 1.5% Pd/activated carbon catalyst. The reaction respectively obtained 66.25 g, 61.49 g, 64.57 g of oily products, and gas chromatography analysis were conducted, the mass content of 2-chloro-5-trifluoromethylpyridine were respectively 85.0%, 89.5%, 89.8%, and the yield were respectively 90.1%, 88.0%, 92.8%.

Example 41

Internal diameter of the heating furnace was 35 mm, the height was 500 mm. The material of the reaction tube was Inconel alloy, the internal diameter of the reaction tube was 30 mm, and the length was 600 mm. The reaction tube was filled with 60 mL of 1% Pd/activated carbon (mean diameter being 0.15 mm) chlorination catalyst, the height of the static bed was 89 mm. After 1 h of fluidization with nitrogen gas at 235° C., the vaporized 3-trifluoromethylpyridine and chlorine gas were introduced into the reaction tube. Wherein, the flowrate of 3-trifluoromethylpyridine was controlled at 6.33 g/h (0.043 mol/h), the flowrate of chlorine gas was controlled at 5.77 L/h (0.258 mol/h), the flowrate of nitrogen gas was maintained at 9.62 L/h (0.430 mol/h). Molar feed ratio of the reactants was 3-trifluoromethylpyridine:chlorine gas=1:6, the contact time of all starting reaction materials with the catalyst bed was 13.5 s, and reacted for 24 h.

The tail gas leaving the reaction tube was introduced into the water washing tower and the alkaline washing tower for condensation. The oil layer obtained was separated then neutralized with aqueous ammonia, and a steam distillation was conducted against the oily product obtained. The oily product obtained was dried on anhydrous sodium sulfate then weighed and the mass was 185.88 g, a quantitative analysis was conducted by gas chromatography internal standard method, the mass content of 2-chloro-5-trifluoromethylpyridine was 95.8%, and the yield was 94.9%.

Example 42

Except that catalyst was different, other condition was same as Example 41. The reaction tube was filled with 60 mL of 1% Pd/Al$_2$O$_3$ (mean diameter being 0.15 mm) chlorination catalyst. The product treatment and analysis method were same as Example 38, to obtain 179.69 g of an oily product, by chromatography analysis the mass content of 2-chloro-5-trifluoromethylpyridine was 94.6%, and the yield was 90.7%.

The above preparing method of 2,3-dichloro-5-trifluoromethylpyridine provided by the present invention significantly increases the yield and the selectivity of the desired product 2,3-dichloro-5-trifluoromethylpyridine. The selectivity of 2,3-dichloro-5-trifluoromethylpyridine can substantially reach at least 82% or more. The method provided by the present invention not only reduces the unit consumption of the product, and reduces separation cost, but also the reaction temperature is much lower than 400° C., the method can significantly reduce energy consumption and improve safety.

The invention claimed is:

1. A method for preparing 2,3-dichloro-5-trifluoromethylpyridine by a pressurized liquid phase chlorination, wherein the method comprises:
   (1) chlorofluorination reaction: in presence of a catalyst for chlorofluorination, the chlorofluorination temperature is maintained at 150~320° C., and 3-methylpyridine, chlorine gas and hydrogen fluoride are introduced into a chlorofluorination reaction region, to obtain a mixed gas comprising 3-trifluoromethylpyridine;
   (2) chlorination reaction: in presence of a chlorination catalyst, the chlorination temperature is maintain at 220~380° C., and the mixed gas comprising 3-trifluoromethylpyridine obtained in step (1) is introduce into a chlorination reaction region, to obtain 2-chloro-5-trifluoromethylpyridine, the chlorination catalyst is selected from fluoride, oxide, hydroxide, carbonate or chloride of magnesium, calcium, barium, a supported palladium catalyst supported on activated carbon, alumina or aluminium fluoride;
   (3) at a temperature of 100~150° C. and a pressure of 0.5~5.0 MPa, in presence of a first catalyst, 2-chloro-5-trifluoromethylpyridine reacts with chlorine gas to obtain 2,3-dichloro-5-trifluoromethylpyridine;
   the first catalyst is supported metal chloride;
   for the supported metal chloride, its active components are at least one selected from WCl$_6$, MoCl$_5$, FeCl$_3$, AlCl$_3$, CuCl$_2$, ZnCl$_2$, SnCl$_4$, and SbCl$_5$, and the load of the active components is 1~50 wt %;
   the carrier used in the first catalyst is at least one selected from silicon dioxide, alumina, titania, zirconia, activated carbon, silicon carbide and mesoporous molecular.

2. The method for preparing 2,3-dichloro-5-trifluoromethylpyridine by a pressurized liquid phase chlorination according to claim 1, wherein the chlorination catalyst is selected from fluoride, oxide or chloride of magnesium, calcium, a supported palladium catalyst supported on activated carbon or aluminium fluoride.

3. The method for preparing 2,3-dichloro-5-trifluoromethylpyridine by a pressurized liquid phase chlorination according to claim 1, wherein the chlorofluorination temperature is 220~260° C., and chlorination temperature is 270~320° C.

4. The method for preparing 2,3-dichloro-5-trifluoromethylpyridine by a pressurized liquid phase chlorination according to claim 1, wherein the chlorofluorination catalyst includes a main catalyst, a first co-catalyst and a second co-catalyst, the main catalyst is at least one selected from aluminium, magnesium and chromium, the first co-catalyst is at least one selected from iron, cobalt, manganese, nickel, copper, bismuth and zinc, the second co-catalyst is at least one selected from lanthanium, cerium, barium, calcium, sodium and potassium, the molar ratio of the main catalyst, the first co-catalyst and the second co-catalyst is 50~95: 5~42:0.3~8.

5. The method for preparing 2,3-dichloro-5-trifluoromethylpyridine by a pressurized liquid phase chlorination according to claim 4, wherein in the chlorofluorination catalyst, the main catalyst is selected from aluminium and/or chromium, the first co-catalyst is at least one selected from iron, nickel and copper, the second co-catalyst is at least one selected from lanthanium, barium and calcium, the molar ratio among the main catalyst, the first co-catalyst and the second co-catalyst is 75~90:10~20:1~5.

6. The method for preparing 2,3-dichloro-5-trifluoromethylpyridine by a pressurized liquid phase chlorination according to claim 1, wherein the molar ratio among the 3-methylpyridine, chlorine gas and hydrogen fluoride is 1:0.1~50:1~30.

7. The method for preparing 2,3-dichloro-5-trifluoromethylpyridine by a pressurized liquid phase chlorination according to claim 6, wherein the molar ratio among the 3-methylpyridine, chlorine gas and hydrogen fluoride is 1:4~10:3~12.

8. The method for preparing 2,3-dichloro-5-trifluoromethylpyridine by a pressurized liquid phase chlorination according to claim 1, wherein the 3-methylpyridine is a mixed gas diluted by an inert gas, and the molar ratio of 3-methylpyridine to the inert gas is 1:0.5~50.

9. The method for preparing 2,3-dichloro-5-trifluoromethylpyridine by a pressurized liquid phase chlorination according to claim 8, wherein the molar ratio of the 3-methylpyridine to the inert gas is 1:5~20.

10. The method for preparing 2,3-dichloro-5-trifluoromethylpyridine by a pressurized liquid phase chlorination according to claim 1, wherein
    in the step (1), the contact time of 3-methylpyridine, chlorine gas and hydrogen fluoride with the chlorofluorination catalyst is 0.5~40 s;
    in the step (2), the contact time of the mixed gas comprising 3-trifluoromethylpyridine with the chlorination catalyst is 0.5~40 s.

11. The method for preparing 2,3-dichloro-5-trifluoromethylpyridine by a pressurized liquid phase chlorination according to claim 10, wherein
    in the step (1), the contact time of 3-methylpyridine, chlorine gas and hydrogen fluoride with the chlorofluorination catalyst is 1.5~20 s;
    in the step (2), the contact time of the mixed gas comprising 3-trifluoromethylpyridine with the chlorination catalyst is 1.5~20 s.

* * * * *